United States Patent [19]

Sackner

[11] Patent Number: 4,679,555

[45] Date of Patent: Jul. 14, 1987

[54] METHOD AND APPARATUS FOR INTRAPULMONARY DELIVERY OF HEPARIN

[75] Inventor: Marvin A. Sackner, Miami Beach, Fla.

[73] Assignee: Key Pharmaceuticals, Inc., Miami, Fla.

[21] Appl. No.: 638,587

[22] Filed: Aug. 7, 1984

[51] Int. Cl.$^4$ ............................................. A61M 15/00
[52] U.S. Cl. ................................... 128/203.15; 604/58
[58] Field of Search ...................... 128/200.23, 200.16, 128/203.15; 604/58

[56] References Cited

U.S. PATENT DOCUMENTS

| | | | |
|---|---|---|---|
| 2,788,784 | 4/1957 | Birch et al. | 128/200.23 |
| 3,404,681 | 10/1968 | Fowler | 128/200.23 |
| 3,727,806 | 4/1973 | Wilmot | 222/402.2 |
| 3,897,779 | 8/1975 | Hanson | 128/203.15 |
| 4,052,985 | 10/1977 | Coleman et al. | 128/200.23 |
| 4,484,577 | 11/1984 | Sackner et al. | 128/203.28 |

FOREIGN PATENT DOCUMENTS 862538 6/1978 Belgium .
13534 7/1980 European Pat. Off. ....... 128/200.23

OTHER PUBLICATIONS

Jaques et al., Intrapulmonary Heparin . . . , The Lancet, Nov. 27, 1976, pp. 1157–1161.
Hellgren et al., Heparin Aerosol . . . , Thrombosis Research, vol. 21, pp. 493–502, 1981.
L. B. Jaques, Heparin: An Old Drug with a New Paradigm, Science, Nov. 1979, vol. 206, pp. 528–533.
Merck Index, Tenth Edition, Entry No. 4543.
U.S. Pharmacopeia National Formulary, 1980, vol. XX, p. 365.

*Primary Examiner*—Henry J. Recla
*Attorney, Agent, or Firm*—Anita W. Magatti; Stephen I. Miller

[57] ABSTRACT

An apparatus comprised of a canister having a valved opening thereon and containing, under pressure, heparin and a low boiling point propellant is disclosed. The valved opening can be activated to release a metered dose of aerosolized heparin to a patient or preferably to an inhalation device which improves efficiency with respect to the amount of heparin reaching the lungs of the patient.

9 Claims, No Drawings

METHOD AND APPARATUS FOR INTRAPULMONARY DELIVERY OF HEPARIN

FIELD OF THE INVENTION

The present invention relates to an apparatus and a method for carrying out intrapulmonary delivery of heparin to a patient. More specifically, the invention relates to a metered dose inhaler device containing heparin and a low boiling point propellant which is preferably used in combination with an inhalation device capable of improving efficiency with respect to the amount of heparin reaching the lungs of a patient.

BACKGROUND OF THE INVENTION

Heparin was introduced to clinical medicine about forty-eight years ago on the basis of experimental work establishing its value in the prevention of venous thrombosis and as an essential aid for successful vascular surgery. For about forty eight years heparin has been used as an essential drug in the diagnosis and treatment of diseases of the heart and blood vessels. It is prepared commercially from beef lung and pork intestinal mucosa. (See Heparin: An Old Drug With A New Paradigm, SCIENCE, November, 1979 Vol. 206 pp. 528–533.)

In 1976, more than nine billion units (six metric tons) of heparin was administered to approximately ten million patients and consumption is believed to have increased yearly since that time. Although heparin is an essential aid for successful vascular surgery, it is not absorbed in the GI tract and thus cannot be administered orally. Accordingly, the drug is generally administered by injection (intravenously or intramuscularly) or subcutaneously.

Strictly speaking heparin is heparinic acid which is a highly sulfated dextrorotatory mucopolysaccharide, having specific anticoagulant properties. Heparinic acid is composed of D-glucosamine and D-glucuronic acid residues. It has a molecular weight which varies from 6,000 to 20,000 depending on the source and method of determination. As used herein, the word heparin will refer to heparinic acid as well as all of the pharmaceutically acceptable salts of heparinic acid. Some of the common salts include calcium salt (calciparine) magnesium salt (magnesium heparinate, cutheparine), potassium salt (clarin) and sodium salt sold under various names including heparin sodium. Sodium salts of heparinic acid are the most commonly used pharmaceutical drug encompassed by the name heparin and such sodium salts make up a white or grayish brown amorphous powder which is odorless and hygroscopic. (See Merck Index, Tenth Edition, Entry No. 4543 which is incorporated herein with respect to its disclosure of heparin and pharmaceutically acceptable salts thereof.)

The most commonly used heparin (heparin sodium) has a potency which is calculated on a dried basis. Its potency is not less than 120 USP heparin units in each mg when derived from lungs and not less than 140 USP heparin units in each mg when derived from other tissues, and not less than 90% and not more than 100% of the potency stated on the label. (See U.S. Pharmacopeia National Formulary 1980 page 365 Vol. XX.)

It was not until 1976, after forty (40) years of using heparin, that researchers realized that it would be possible to deliver heparin via an intrapulmonary route. (See Jaques, et al "Intrapulmonary Heparin, A New Procedure for Anticoagulant Therapy", The Lancet, November 27, 1976 p. 1157–1161.) These researchers utilized a "DeVilbiss ultrasonic nebuliser which contained a volume of 10 to 20 mg heparin per milliliter. In order to administer the heparin, the subjects were instructed to take slow deep breaths for periods of five minutes with rest intervals of one to two minutes for a total time of one and a half hours. The test results of intrapulmonary administration of heparin contrast strikingly with the results obtained with intravenous or subcutaneous heparin in doses of 140 to 150 units per kilogram which produced incoagulability for a short time. With intravenous anticoagulants, prolongation of effect accompanies increased hypocoagulability. After intrapulmonary heparin, the effects last much longer and the hypocoagulability is more moderate. Accordingly, the results obtained utilizing the nebuliser were clearly advantageous. However, in order to obtain these effects the patients were required to inhale heparin from a nebuliser over an extended period of time. Therefore, it could be concluded that although benefits are obtained from the intrapulmonary delivery of heparin, such a delivery means is often too inconvenient for the patient to utilize.

Belgian patent 862,538 discloses the intrapulmonary delivery of heparin wherein sodium heparin is included in an aqueous solution and provided in an aerosol form by means of a nebuliser. The patent specifically discloses the inclusion of an agent for increasing the permeability of heparin through the lung alveoli and bronchial mucosa.

Another study relating to the intrapulmonary delivery of heparin is "Heparin Aerosol - Effect on Blood Coagulation and Pulmonary Function," Hellgren, et al., Thrombosis Research 21; 493-502 Pergamon Press Ltd 1981. A "modified" deVilbiss ultrasonic nebuliser is used for administration which is disclosed as requiring 60–90 minutes. These researchers also recognized that the molecular weight of the heparin administered might have an affect on absorbtion.

Since 1976 researchers have investigated the possibility of intrapulmonary delivery of heparin. However, it appears as though each attempt involves either the use of a nebuliser or direct intratracheal installation. The use of a nebuliser requires a long period of time and is expensive due to the cost of medical personnel required as well as the equipment and the heparin lost by this inefficient means of administration. The use of intratracheal installation generally requires that the patient be anesthetized which increases both the cost and risks involved in administration. Although tests show that heparin may be administered by the intrapulmonary route without toxicity, this means of administration has not been generally accepted because administration by injection is less expensive, safer and more convenient.

SUMMARY OF INVENTION

A primary object of the present invention is to provide a method of intrapulmonary administration of heparin.

Another object of the invention is to provide such a method which comprises releasing a metered burst of aerosolized heparin from a pressurized canister containing heparin and a low boiling point propellant, inhaling the metered burst of aerosolized heparin into the lungs of a patient and repeating the releasing and inhaling steps until a pharmaceutically effective amount of the heparin has been administered to the patient.

Yet another object of the invention is to provide such, a method wherein the metered burst is released to an inhalation device capable of improving efficiency with respect to the amount of heparin reaching the lungs of the patient and further wherein the inhaling is from the inhalation device.

Another method is to provide an apparatus comprised of a canister having a valved opening thereon and containing; under pressure, heparin and a low boiling point propellant.

Still another object of the invention is to provide such an apparatus wherein the valved opening is capable of releasing a metered dose of aerosolized heparin upon actuation.

Still another object of the invention is to provide such an apparatus wherein the valved opening is in connection with an inhalation device capable of improving efficiency with respect to the amount of heparin reaching the lungs of a patient.

Still another object of the invention is to provide a complete intrapulmonary heparin administration kit comprised of a canister having a valved opening thereon and containing, under pressure, heparin and a low boiling point propellant, an inhalation device which can be used in combination with the canister, and instructions describing the use of the canister in combination with the inhalation device in order to provide a pharmaceutically effective dose of heparin to a patient via the intrapulmonary delivery route.

Yet another object of the invention is to provide an inexpensive means of intrapulmonary delivery of heparin.

Another object of the invention is to provide a safe means of intrapulmonary delivery of heparin by which the dose administered can be precisely regulated.

These and other objects of the invention will become apparent to those skilled in the art upon reading this disclosure.

DETAILED DESCRIPTION OF THE INVENTION

As discussed above, intrapulmonary delivery of heparin is possible, although inconvenient. The present invention involves a convenient means and apparatus for carrying out the intrapulmonary delivery of heparin. The present invention utilizes a metered dose inhaler (hereinafter MDI) by itself or in combination with an inhalation device which improves efficiency with respect to the amount of heparin reaching the lungs of the patient. By utilizing such an MDI alone or in combination with an inhalation device, it is possible to greatly improve the efficiency of intrapulmonary delivery of heparin as opposed to the use of a nebuliser containing heparin and to eliminate the need for anesthetization required for intratracheal installation of heparin. The MDI makes it possible to more precisely regulate the amount of heparin delivered as compared with delivery via a nebuliser.

The use of MDI's for the intrapulmonary delivery of various medicaments is well known. The structure and basic make-up of such MDI's is fairly standard although there is some variation with respect to some minor features of the valves and nozzles (see U.S. Pat. No. 3,727,806 incorporated herein by reference to disclose an MDI). Since the essence of the invention disclosed herein does not relate specifically to the structure of an MDI device, the details of their construction will not be discussed herein. Means of making and using MDI's are known to those skilled in the art. However, it should be pointed out that MDI's are basically comprised of pressurized canisters having valved openings thereon. Upon actuation of the valve a metered dose is released from the canister. (That this dose can be accurately measured is a feature of the present invention in that prior art intrapulmonary delivery means do not allow for such accuracy.) The canister contains a propellant in combination with a medicament which may be dissolved in the propellant or dispersed within it. Propellants which are utilized within such MDI devices are referred to generally as low boiling point propellants. Useful propellants include various types of hydrocarbons, fluorocarbons and chlorocarbons. Low boiling hydrocarbons have disadvantages due to their flammability and fluorocarbons have met with objection from environmentalists. Specific examples of presently used propellants include trichloromonofluoromethane and dichlorodifluoromethane. The use of such propellants in combination with heparin are a feature of the present invention in that they allow for more efficient and economical delivery of heparin.

While these propellants are held within the pressurized canister of the MDI the propellants are maintained in a liquid state. When the valve of the MDI is actuated, the propellant is released and forces medicament from the canister along with the propellant. When a metered dose or burst is fired from the MDI, the liquid propellant and medicament rush out from the nozzle of the canister. Upon exposure to the lower pressure of the surrounding atmosphere, a proportion of the propellants flash, i.e. are immediately vaporized. This flashing occurs so rapidly that the heat required from the change of phase from liquid to gas is taken from the remainder of the propellant. The remaining liquid propellant droplets are cooled down. Further evaporation of the liquid droplets occurs during passage through the air, as energy is acquired from the surrounding atmosphere. This rate of evaporation is comparatively low with respect to the initial flashing. However, it occurs rapidly thus leaving the medicament, essentially by itself, to be delivered to the patient.

When utilizing conventional nebulisers, no flashing and/or evaporation of the surrounding propellant takes place. Accordingly, the droplets and/or particles which are delivered to the patient contain large amounts of materials other than the medicament and the droplet particles have a substantially larger size. Since the particles have a larger size, they are less likely to be inhaled into the lungs but rather are deposited on the mucosa of the mouth and throat. By utilizing the MDI device, the particles which enter the patient's mouth are essentially pure medicament and these particles are of such a small size that greater numbers of the particles be completely inhaled into the lungs.

As indicated above, when the valve of an MDI is actuated a quick burst of medicament dispersed within a propellant is released from the nozzle. If the patient has not timed this actuation with an inhalation, a large number of the particles may also be deposited on the mucosa of the mouth and throat and thus not drawn into the lungs. To aid in avoiding this problem, it is possible to use an inhalation device in combination with the MDI which improves efficiency with respect to the amount of medicament reaching the lungs of the patient. Such a device is disclosed, by the present inventor in U.S. Pat. No. 4,484,577. The device disclosed within this patent is incorporated herein by reference for disclosing such an inhalation device. By utilizing such an inhalation device in combination with an MDI, it is possible to increase the efficiency of medicament delivered to the patient by a factor of 3 to 4 times.

For the reasons put forth above, the use of an MDI can be 10 to 30 times more efficient than a conventional nebuliser with respect to the delivery of medicament to the lungs of a patient. As further indicated above, the efficiency of an MDI can be increased 3 to 4 times by using such an MDI in combination with known inhalation devices. The inhalation device described within U.S. Pat. No. 4,484,577 is now sold under the trademark "Inspirease".

Accordingly, the present invention involves including heparin within the propellant of an MDI and utilizing that MDI by itself or in combination with an inhalation device to provide for efficient intrapulmonary delivery of heparin.

As indicated above, heparin is commonly sold in the form of a sodium salt which is a white to grayish brown amorphous powder. This powder can be ground into fine particles which make up a dust which can then be dispersed in a low boiling point propellant such as commonly used low boiling point chlorofluoroalkanes. The propellant having the sodium heparin dispersed therein is included within a canister under pressure. The canister has a valve thereon which when actuated allows for the release of a metered dose of the contents.

The metered dose or burst which is released from the canister can be inhaled directly by a patient. However, in order to increase the efficiency of the sodium heparin which will reach the lungs of the patient, it is preferable to release the dose into an inhalation device which is capable of increasing efficiency with respect to the amount of sodium heparin reaching the lungs of the patient. In order to decrease the time needed for delivery, more than one burst can be released into the device. The burst or bursts released into the inhalation device form a cloud of heparin dust which is then drawn from this device by the inhaling patient in order to draw particles of the sodium heparin into the lungs of the patient. By directing the metered dose into the inhalation device, essentially all of the low boiling point propellant evaporates away leaving only the dust particles of sodium heparin to be inhaled by the patient.

An effective dose of pulmonary heparin capable of giving a measurable anticoagulant response in man has been determined to be between 12 to 18 mg/kg. Converting a 15 mg/kg dose into units for comparison, this amounts to 1050 mg for a 70 kg man.

By utilizing a nebuliser, it is possible to deliver an effective dose of sodium heparin to a patient. A great deal of the material delivered to the lungs per inhalation is not heparin but rather propellant necessary to aerosolize the sodium heparin. Accordingly, by utilizing a nebuliser for the intrapulmonary delivery of heparin, the patient must take inhalations for 60 to 90 minutes in order to receive an effective dose which provides a measurable anticoagulant response (see Hellgren, et al., cited above).

By utilizing a MDI in accordance with the present invention, the sodium heparin dust is dispersed within the low boiling point propellant. Upon the release of a metered dose, much of the propellant flashes immediately and the remainder evaporates rather quickly making it possible to deliver 10 to 30 times as much sodium heparin per inhalation to the lungs of a patient as compared to the use of a nebuliser. Assuming a fifteen fold increase in efficiency, a patient would only need to have seventy (70) inhalations in order to receive an effective dose which provides a measurable anticoagulant response (again assuming a seventy (70) kilogram person). If we assume five (5) inhalations per minute, an effective dose can be delivered in about 14 minutes.

As also indicated above, it is possible to increase the efficiency of the MDI by utilizing it in connection with an inhalation device such as disclosed in U.S. Pat. No. 4,484,577. The use of such a device in combination with the MDI increases the efficiency of the MDI with respect to the amount of heparin reaching the lungs of the patient by a factor of 3 to 4 times. Assuming an increase in efficiency of 3.5 times, a patient could receive a pharmaceutically effective amount of sodium heparin by taking only twenty (20) inhalations. Assuming the same five (5) inhalations per minute, an effective dose could be delivery in about four minutes. It would be possible to further reduce the number of inhalation needed and the time required to administer an effective dose by including more than one dose or burst from the MDI in the inhalation device prior to each inhalation.

In accordance with a particularly preferred embodiment of the invention, a complete intrapulmonary heparin administration kit is provided. The kit includes an MDI which is comprised of a pressurized canister having powdered sodium heparin dispersed within a propellant contained therein, an inhalation device which improves efficiency of the MDI with respect to the amount of sodium heparin reaching the lungs and specific medical instructions with respect to how to use the MDI by itself and/or in combination with the inhalation device in order to provide a pharmaceutically effective amount of heparin to the patient. The canister may have various sizes but is resently contemplated as containing 200–300 mg of heparin.

It was indicated above that by using the MDI of the present invention, the efficiency of intrapulmonary heparin could be increased by a factor of 10 to 30 times as compared with the use of a nebuliser. Further, it was indicated that the efficiency of the MDI of the present invention could be further improved by a factor of 3 to 4 times by utilizing that MDI in connection with an inhalation device. Accordingly, assuming a three fold increase in efficiency with such a device, the total increase in efficiency would be in the range of 3 to 90 times and if an increase in efficiency of four fold is assumed, the total increase in efficiency is in the range of 40 to 120 times as compared with the use of a nebuliser. The increase in efficiency is given in terms of ranges due largely to how effectively the patient makes use of the various devices. The effectiveness of the patient in utilizing any intrapulmonary drug delivery means of heparin would be likely to vary over similar ranges regardless of whether the patient was utilizing a nebuliser or an MDI. However, due to the simplicity with which inhalation devices can be utilized the effectiveness of the intrapulmonary delivery of medicaments is generally better and more uniform with such devices. A detailed discussion on the use and misuse of MDIs alone or in combination with inhalation devices is contained within U.S. Pat. No. 4,484,577.

There is a finite amount of heparin available in the world and shortages are not unknown. Further, the drug is relatively expensive. The increased efficiency provided by the present invention would conserve heparin as compared with administration via a nebuliser and also reduce costs. The costs of administering heparin via the present invention are also substantially reduced in that self-administration with a simple inexpensive device is possible.

It was indicated above that the molecular weight of heparin may vary from 6,000 to 12,000 depending on the source and method of determination. It is believed that by administering lower molecular weight heparin, the desired pharmaceutical effects of the heparin per weight amount of heparin administered can be increased. As indicated by Hellgren, et al. (cited above) this is believed to be especially true with respect to intrapulmonary delivery since molecular weight might affect absorption. Accordingly, it is likely that the efficiency of the present invention could be further improved by providing a lower molecular weight heparin in the form of sodium salt within the pressurized canister.

The ability of heparin and heparinoids to form complexes with proteins and enzymes and change the activity of these substances contributes to heparin having a wide range of effects in vivo. Many of these effects are produced with relatively small amounts of heparin or heparinoids, sometimes less than the amount required for an anticoagulant effect. The formation of complexes with body constituents increases the electronegativity of cells. Accordingly, the pharmaceutically effective dose of heparin delivered by any mechanism might vary depending upon the effect desired. Therefore, with the present invention, it may not be necessary to administer the above referred to twenty (20) inhalations of aerosolized heparin in order to obtain the desired results.

Other clinical uses in myocardial infarction and inflammatory and allergic conditions are based on the effect of heparin on enzyme release (lipoprotein lipases) and inhibition and on its ability to block toxic agents, chemicals, viruses, histamine and reduce inflammation. These uses may require higher than usual doses of the anionic polyelectrolyte and for this heparin of low anticoagulant activity in vitro would probably be best. It is evident that the anticoagulant activity of heparin is just one factor in its clinical and biological actions and, in fact, is undesirable in commercial heparin because it increases the hemorrhagic tendency. Accordingly, the physician prescribing the heparin must make a medical determination as to the dose which the patient should receive based on the particular type of heparin used and the means of administering the heparin.

With respect to the heparin which reaches the lungs, it has been determined that about 50% of the heparin is cleared from the lungs within one and half hours and that 90% is cleared from the lungs within twenty-four (24) hours after administration. After administration of the heparin in a sufficient amount, the whole blood coagulation time (WBCT) increases moderately by about 50% but lasts for as much as fourteen (14) days. The extended period of time which the effect of the heparin lasts must be considered before administration of an additional dosage.

Since the increase in the WBCT lasts for up to fourteen (14) days, it may become necessary to counteract the anticoagulation effects of the heparin. This can be done by the administration of protamine. However, it should be noted that the counteracting effect of the protamine wears off more quickly than the anticoagulant effect of the heparin. Consequently repeated administration of protamine may be necessary to continually counteract the long acting anticoagulant action of heparin. The protamine can be administered intravenously and is titrated with respect to the plasma heparin concentration (PHC).

While the invention has been described in detail with reference to specific embodiments thereof, it will be apparent to one skilled in the art that various changes and modifications can be made therein without departing from the spirit and scope thereof.

What is claimed is:

1. An apparatus for the intrapulmonary delivery of heparin, comprising:
   an air tight canister having a valve opening thereon;
   powdered heparin and a low boiling point propellant contained within the canister; and
   means for releasing a metered dose of aerosolized powdered heparin from the container.

2. An apparatus as claimed in claim 1, wherein the valved opening of the canister is in communication with an inhalation device capable of improving the efficiency 3. An intrapulmonary heparin administration kit, comprising:
   a metered dose inhaler device comprised of a canister having a valved opening thereon, the canister containing a low boiling point propellant and powdered heparin;
   an inhalation device which is connectable to the valved opening of the metered dose inhaler;
   instructions with respect to the use of the metered dose inhaler and inhalation device in order to provide a pharmaceutically effect amount of heparin to a patient.

4. The apparatus of claim 1, wherein the powdered heparin is in the form of a pharmaceutically acceptable salt, ground into a fine dust.

5. The apparatus of claim 1, wherein the propellant is a low boiling point chlorofluoroalkane.

6. A method of intrapulmonary administration of heparin, comprising the steps of:
   releasing a metered dose of aerosolized powdered heparin from a pressurized canister containing powdered heparin and a low boiling point propellant;
   inhaling the metered dose of aerosolized powdered heparin into the lungs of a patient;
   repeating the releasing and inhaling steps until a pharmaceutically effective amount of the heparin has been delivered to the patient.

7. A method of administration as claimed in claim 6, wherein the metered dose is released to an inhalation device capable of increasing the efficiency of the administration of aerosolized powdered heparin to the lungs and wherein the inhaling is from the inhalation device.

8. A method as claimed in claim 6, wherein the powdered heparin is in the form of a pharmaceutically acceptable salt ground into fine particles so as to form a dust.

9. A method of administration as claimed in claim 8, wherein the propellant is a low boiling point chlorofluoroalkane.

* * * * *